United States Patent
Unger et al.

(10) Patent No.: US 7,877,853 B2
(45) Date of Patent: Feb. 1, 2011

(54) METHOD OF MANUFACTURING END EFFECTOR ASSEMBLY FOR SEALING TISSUE

(75) Inventors: Jeffrey R. Unger, Longmont, CO (US); Robert M. Sharp, Boulder, CO (US); David W. Hixson, Longmont, CO (US); Chelsea Shields, Portland, OR (US); Darion Peterson, Boulder, CO (US); Jeremy James, Highlands Ranch, CO (US); David M. Garrison, Longmont, CO (US); Michael R. Warzecha, Longmont, CO (US); Edward M. Chojin, Boulder, CO (US); Duane E. Kerr, Berthoud, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 162 days.

(21) Appl. No.: 12/234,128

(22) Filed: Sep. 19, 2008

(65) Prior Publication Data

US 2009/0082769 A1    Mar. 26, 2009

Related U.S. Application Data

(60) Provisional application No. 60/994,551, filed on Sep. 20, 2007.

(51) Int. Cl.
*H01S 4/00* (2006.01)
(52) U.S. Cl. .......................... 29/592.1; 29/825; 29/874; 29/876; 606/49; 606/30; 606/51
(58) Field of Classification Search ............... 29/592.1, 29/825, 874, 876; 606/49, 50, 51
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,852,542 A | 4/1932 | Sovatkin |

(Continued)

FOREIGN PATENT DOCUMENTS

CA    2104423    2/1994

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner*—C. J Arbes

(57) ABSTRACT

A method for manufacturing an end effector assembly for sealing tissue includes the initial step of providing first and second electrically conductive sealing plates. The method also includes the steps of: encasing at least one of the electrically conductive sealing plates in a substantially moldable insulative material; applying a load to the electrically conductive sealing plates; allowing the insulative material to deform to create a gap between the sealing plates between about 0.001 inches to about 0.010 inches; and allowing the insulative material to cure.

4 Claims, 5 Drawing Sheets

U.S. PATENT DOCUMENTS

| | | |
|---|---|---|
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 4/1941 | Grubel |
| 2,279,753 A | 4/1942 | Knopp |
| 2,632,661 A | 8/1948 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,047,046 A | 9/1991 | Bodoia |
| 5,084,057 A | 1/1992 | Green et al. |
| 5,085,659 A | 2/1992 | Rydell |
| 5,099,840 A | 3/1992 | Goble et al. |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Heidmueller nee Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |

| | | | | | |
|---|---|---|---|---|---|
| 5,422,567 A | 6/1995 | Matsunaga | 5,647,869 A | 7/1997 | Goble et al. |
| 5,423,810 A | 6/1995 | Goble et al. | 5,647,871 A | 7/1997 | Levine et al. |
| 5,425,690 A | 6/1995 | Chang | 5,649,959 A | 7/1997 | Hannam et al. |
| 5,425,739 A | 6/1995 | Jessen | 5,655,650 A | 8/1997 | Naitou |
| 5,429,616 A | 7/1995 | Schaffer | 5,658,281 A | 8/1997 | Heard |
| 5,431,672 A | 7/1995 | Cote et al. | D384,413 S | 9/1997 | Zlock et al. |
| 5,431,674 A | 7/1995 | Basile et al. | 5,662,667 A | 9/1997 | Knodel |
| 5,437,292 A | 8/1995 | Kipshidze et al. | 5,665,100 A | 9/1997 | Yoon |
| 5,438,302 A | 8/1995 | Goble | 5,667,526 A | 9/1997 | Levin |
| 5,441,517 A | 8/1995 | Kensey et al. | 5,674,220 A | 10/1997 | Fox et al. |
| 5,443,463 A | 8/1995 | Stern et al. | 5,681,282 A | 10/1997 | Eggers et al. |
| 5,443,464 A | 8/1995 | Russell et al. | 5,688,270 A | 11/1997 | Yates et al. |
| 5,443,480 A | 8/1995 | Jacobs et al. | 5,693,051 A | 12/1997 | Schulze et al. |
| 5,445,638 A | 8/1995 | Rydell et al. | 5,693,920 A | 12/1997 | Maeda |
| 5,445,658 A | 8/1995 | Durrfeld et al. | 5,695,522 A | 12/1997 | LeMaire, III et al. |
| 5,451,224 A | 9/1995 | Goble et al. | 5,700,261 A | 12/1997 | Brinkerhoff |
| 5,456,684 A | 10/1995 | Schmidt et al. | 5,700,270 A | 12/1997 | Peyser et al. |
| 5,458,598 A | 10/1995 | Feinberg et al. | 5,702,390 A | 12/1997 | Austin et al. |
| 5,460,629 A | 10/1995 | Shlain et al. | 5,707,369 A | 1/1998 | Vaitekunas et al. |
| 5,461,765 A | 10/1995 | Linden et al. | 5,709,680 A | 1/1998 | Yates et al. |
| 5,462,546 A | 10/1995 | Rydell | 5,716,366 A | 2/1998 | Yates |
| 5,472,442 A | 12/1995 | Klicek | 5,720,744 A | 2/1998 | Eggleston et al. |
| 5,472,443 A | 12/1995 | Cordis et al. | 5,722,421 A | 3/1998 | Francese et al. |
| 5,478,351 A | 12/1995 | Meade et al. | 5,725,536 A | 3/1998 | Oberlin et al. |
| 5,480,409 A | 1/1996 | Riza | 5,727,428 A | 3/1998 | LeMaire, III et al. |
| 5,484,436 A | 1/1996 | Eggers et al. | 5,735,848 A | 4/1998 | Yates et al. |
| 5,496,312 A | 3/1996 | Klicek | 5,743,906 A | 4/1998 | Parins et al. |
| 5,496,317 A | 3/1996 | Goble et al. | 5,755,717 A | 5/1998 | Yates et al. |
| 5,496,347 A | 3/1996 | Hashiguchi et al. | 5,766,130 A | 6/1998 | Selmonosky |
| 5,499,997 A | 3/1996 | Sharpe et al. | 5,766,166 A | 6/1998 | Hooven |
| 5,509,922 A | 4/1996 | Aranyi et al. | 5,766,170 A | 6/1998 | Eggers |
| 5,512,721 A | 4/1996 | Young et al. | 5,769,849 A | 6/1998 | Eggers |
| 5,514,134 A | 5/1996 | Rydell et al. | 5,772,655 A | 6/1998 | Bauer et al. |
| 5,527,313 A | 6/1996 | Scott et al. | 5,772,670 A | 6/1998 | Brosa |
| 5,529,067 A | 6/1996 | Larsen et al. | 5,776,128 A | 7/1998 | Eggers |
| 5,531,744 A | 7/1996 | Nardella et al. | 5,776,130 A | 7/1998 | Buysse et al. |
| 5,536,251 A | 7/1996 | Evard et al. | 5,779,701 A | 7/1998 | McBrayer et al. |
| 5,540,684 A | 7/1996 | Hassler, Jr. | H1745 H | 8/1998 | Paraschac |
| 5,540,685 A | 7/1996 | Parins et al. | 5,792,137 A | 8/1998 | Carr et al. |
| 5,540,715 A | 7/1996 | Katsaros et al. | 5,792,177 A | 8/1998 | Kaseda |
| 5,542,945 A | 8/1996 | Fritzsch | 5,797,927 A | 8/1998 | Yoon |
| 5,558,671 A | 9/1996 | Yates | 5,797,938 A | 8/1998 | Paraschac et al. |
| 5,558,672 A | 9/1996 | Edwards et al. | 5,797,941 A | 8/1998 | Schulze et al. |
| 5,562,699 A | 10/1996 | Heimberger et al. | 5,797,958 A | 8/1998 | Yoon |
| 5,562,720 A | 10/1996 | Stern et al. | 5,800,449 A | 9/1998 | Wales |
| 5,569,241 A | 10/1996 | Edwardds | 5,807,393 A | 9/1998 | Williamsom, IV et al. |
| 5,569,243 A | 10/1996 | Kortenbach et al. | 5,810,805 A | 9/1998 | Sutcu et al. |
| 5,571,100 A | 11/1996 | Goble et al. | 5,810,808 A | 9/1998 | Eggers |
| 5,573,424 A | 11/1996 | Poppe | 5,810,811 A | 9/1998 | Yates et al. |
| 5,573,534 A | 11/1996 | Stone | 5,810,877 A | 9/1998 | Roth et al. |
| 5,573,535 A | 11/1996 | Viklund | 5,814,043 A | 9/1998 | Shapeton |
| 5,575,805 A | 11/1996 | Li | 5,817,093 A | 10/1998 | Williamson, IV et al. |
| 5,578,052 A | 11/1996 | Koros et al. | 5,820,630 A | 10/1998 | Lind |
| 5,579,781 A | 12/1996 | Cooke | 5,827,271 A | 10/1998 | Buysse et al. |
| 5,582,611 A | 12/1996 | Tsukagoshi et al. | 5,827,279 A | 10/1998 | Hughett et al. |
| 5,585,896 A | 12/1996 | Yamazaki et al. | 5,827,281 A | 10/1998 | Levin |
| 5,590,570 A | 1/1997 | LeMaire, III et al. | 5,827,323 A | 10/1998 | Klieman et al. |
| 5,597,107 A | 1/1997 | Knodel et al. | 5,827,548 A | 10/1998 | Lavallee et al. |
| 5,601,601 A | 2/1997 | Tal et al. | 5,833,690 A | 11/1998 | Yates et al. |
| 5,601,641 A | 2/1997 | Stephens | 5,843,080 A | 12/1998 | Fleenor et al. |
| 5,603,711 A | 2/1997 | Parins et al. | 5,849,022 A | 12/1998 | Sakashita et al. |
| 5,603,723 A | 2/1997 | Aranyi et al. | 5,853,412 A | 12/1998 | Mayenberger |
| 5,611,798 A | 3/1997 | Eggers | 5,859,527 A | 1/1999 | Cook |
| 5,611,808 A | 3/1997 | Hossain et al. | 5,860,976 A | 1/1999 | Billings et al. |
| 5,620,453 A | 4/1997 | Nallakrishnan | 5,876,401 A | 3/1999 | Schulze et al. |
| 5,620,459 A | 4/1997 | Lichtman | 5,882,567 A | 3/1999 | Cavallaro et al. |
| 5,624,452 A | 4/1997 | Yates | 5,891,141 A | 4/1999 | Rydell |
| 5,626,578 A | 5/1997 | Tihon | 5,891,142 A | 4/1999 | Eggers et al. |
| 5,626,609 A | 5/1997 | Zvenyatsky et al. | 5,893,863 A | 4/1999 | Yoon |
| 5,630,833 A | 5/1997 | Katsaros et al. | 5,893,875 A | 4/1999 | O'Connor et al. |
| 5,637,110 A | 6/1997 | Pennybacker et al. | 5,893,877 A | 4/1999 | Gampp, Jr. et al. |
| 5,638,003 A | 6/1997 | Hall | 5,902,301 A | 5/1999 | Olig |
| 5,643,294 A | 7/1997 | Tovey et al. | 5,906,630 A | 5/1999 | Anderhub et al. |

| Patent No. | Date | Inventor |
|---|---|---|
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,938 A | 11/1999 | Yoon |
| 5,984,939 A | 11/1999 | Yoon |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka et al. |
| 6,024,741 A | 2/2000 | Williamson et al. |
| 6,024,743 A | 2/2000 | Edwards |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,500,176 B1 | 12/2002 | Truckai et al. |
| 6,508,815 B1 | 1/2003 | Strul et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,669,696 B2 | 12/2003 | Bacher et al. |
| 6,673,092 B1 | 1/2004 | Bacher |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |

| | | | | | | |
|---|---|---|---|---|---|---|
| 6,685,724 B1 | 2/2004 | Haluck | | 7,101,373 B2 | 9/2006 | Dycus et al. |
| 6,689,131 B2 | 2/2004 | McClurken | | 7,103,947 B2 | 9/2006 | Sartor et al. |
| 6,692,445 B2 | 2/2004 | Roberts et al. | | 7,112,199 B2 | 9/2006 | Cosmescu |
| 6,693,246 B1 | 2/2004 | Rudolph et al. | | D531,311 S | 10/2006 | Guerra et al. |
| 6,695,840 B2 | 2/2004 | Schulze | | 7,115,123 B2 | 10/2006 | Knowlton et al. |
| 6,702,810 B2 | 3/2004 | McClurken et al. | | 7,118,570 B2 | 10/2006 | Tetzlaff et al. |
| 6,723,092 B2 | 4/2004 | Brown et al. | | 7,118,587 B2 | 10/2006 | Dycus et al. |
| 6,726,068 B2 | 4/2004 | Miller | | 7,131,860 B2 | 11/2006 | Sartor et al. |
| 6,726,686 B2 | 4/2004 | Buysse et al. | | 7,131,970 B2 | 11/2006 | Moses et al. |
| 6,726,694 B2 | 4/2004 | Blatter et al. | | 7,131,971 B2 | 11/2006 | Dycus et al. |
| 6,733,498 B2 | 5/2004 | Paton et al. | | 7,135,020 B2 | 11/2006 | Lawes et al. |
| 6,736,813 B2 | 5/2004 | Yamauchi et al. | | D533,942 S | 12/2006 | Kerr et al. |
| 6,743,229 B2 | 6/2004 | Buysse et al. | | 7,145,757 B2 | 12/2006 | Shea et al. |
| 6,743,230 B2 | 6/2004 | Lutze et al. | | 7,147,638 B2 * | 12/2006 | Chapman et al. ............... 606/51 |
| 6,756,553 B1 | 6/2004 | Yamaguchi et al. | | 7,150,097 B2 | 12/2006 | Sremcich et al. |
| 6,757,977 B2 | 7/2004 | Dambal et al. | | 7,150,749 B2 | 12/2006 | Dycus et al. |
| D493,888 S | 8/2004 | Reschke | | D535,027 S | 1/2007 | James et al. |
| 6,770,072 B1 | 8/2004 | Truckai et al. | | 7,156,842 B2 | 1/2007 | Sartor et al. |
| 6,773,409 B2 | 8/2004 | Truckai et al. | | 7,156,846 B2 | 1/2007 | Dycus et al. |
| 6,773,434 B2 | 8/2004 | Ciarrocca | | 7,160,298 B2 | 1/2007 | Lawes et al. |
| 6,775,575 B2 | 8/2004 | Bommannan et al. | | 7,160,299 B2 * | 1/2007 | Baily .......................... 606/51 |
| 6,776,780 B2 | 8/2004 | Mulier et al. | | 7,169,146 B2 | 1/2007 | Truckai et al. |
| 6,786,905 B2 | 9/2004 | Swanson et al. | | 7,179,258 B2 | 2/2007 | Buysse et al. |
| 6,790,217 B2 | 9/2004 | Schulze et al. | | 7,195,631 B2 | 3/2007 | Dumbauld |
| 6,796,981 B2 | 9/2004 | Wham et al. | | D541,418 S | 4/2007 | Schechter et al. |
| D496,997 S | 10/2004 | Dycus et al. | | 7,207,990 B2 | 4/2007 | Lands et al. |
| 6,800,825 B1 | 10/2004 | Sasaki et al. | | D541,938 S | 5/2007 | Kerr et al. |
| 6,802,843 B2 | 10/2004 | Truckai et al. | | 7,223,265 B2 | 5/2007 | Keppel |
| 6,808,525 B2 | 10/2004 | Latterell et al. | | 7,232,440 B2 | 6/2007 | Dumbauld et al. |
| D499,181 S | 11/2004 | Dycus et al. | | 7,241,288 B2 | 7/2007 | Braun |
| 6,818,000 B2 | 11/2004 | Muller et al. | | 7,241,296 B2 | 7/2007 | Buysse et al. |
| 6,857,357 B2 | 2/2005 | Fujii | | 7,244,257 B2 | 7/2007 | Podjahsky et al. |
| 6,860,880 B2 | 3/2005 | Treat et al. | | 7,246,734 B2 | 7/2007 | Shelto, IV |
| 6,887,240 B1 | 5/2005 | Lands et al. | | 7,252,667 B2 | 8/2007 | Moses et al. |
| 6,908,463 B2 * | 6/2005 | Treat et al. .................... 606/29 | | 7,255,697 B2 | 8/2007 | Dycus et al. |
| 6,914,201 B2 | 7/2005 | Van Vooren et al. | | 7,267,677 B2 | 9/2007 | Johnson et al. |
| 6,926,716 B2 | 8/2005 | Baker et al. | | 7,270,660 B2 | 9/2007 | Ryan |
| 6,929,644 B2 | 8/2005 | Truckai et al. | | 7,270,664 B2 | 9/2007 | Johnson et al. |
| 6,932,810 B2 | 8/2005 | Ryan | | 7,276,068 B2 | 10/2007 | Johnson et al. |
| 6,932,816 B2 | 8/2005 | Phan | | 7,300,435 B2 | 11/2007 | Wham et al. |
| 6,934,134 B2 | 8/2005 | Mori et al. | | 7,303,557 B2 | 12/2007 | Wham et al. |
| 6,936,061 B2 | 8/2005 | Sasaki | | 7,311,709 B2 | 12/2007 | Truckai et al. |
| D509,297 S | 9/2005 | Wells | | 7,314,471 B2 | 1/2008 | Holman |
| 6,942,662 B2 | 9/2005 | Goble et al. | | 7,329,256 B2 | 2/2008 | Johnson et al. |
| 6,943,311 B2 | 9/2005 | Miyako | | 7,329,257 B2 | 2/2008 | Kanehira et al. |
| 6,953,430 B2 | 10/2005 | Kidooka | | D564,662 S | 3/2008 | Moses et al. |
| 6,953,461 B2 | 10/2005 | McClurken et al. | | 7,338,526 B2 | 3/2008 | Steinberg |
| 6,958,070 B2 | 10/2005 | Witt et al. | | 7,342,754 B2 | 3/2008 | Fitzgerald et al. |
| 6,960,210 B2 | 11/2005 | Lands et al. | | 7,344,268 B2 | 3/2008 | Jhigamian |
| 6,964,662 B2 | 11/2005 | Kidooka | | D567,943 S | 4/2008 | Moses et al. |
| 6,966,907 B2 | 11/2005 | Goble | | 7,367,976 B2 | 5/2008 | Lawes et al. |
| 6,977,495 B2 | 12/2005 | Donofrio | | 7,377,920 B2 | 5/2008 | Buysse et al. |
| 6,979,786 B2 | 12/2005 | Aukland et al. | | 7,384,420 B2 | 6/2008 | Dycus et al. |
| 6,987,244 B2 | 1/2006 | Bauer | | 7,384,421 B2 | 6/2008 | Hushka |
| 6,994,707 B2 | 2/2006 | Ellman et al. | | 7,396,265 B2 * | 7/2008 | Darley et al. ................. 439/885 |
| 6,994,709 B2 | 2/2006 | Iida | | 7,396,356 B2 * | 7/2008 | Mollenauer ................... 606/51 |
| 7,011,657 B2 | 3/2006 | Truckai et al. | | D575,395 S | 8/2008 | Hushka |
| 7,033,354 B2 | 4/2006 | Keppel | | D575,401 S | 8/2008 | Hixson et al. |
| 7,033,356 B2 | 4/2006 | Latterell et al. | | 7,435,249 B2 | 10/2008 | Buysse et al. |
| 7,041,102 B2 | 5/2006 | Truckai et al. | | 7,442,193 B2 | 10/2008 | Shields et al. |
| 7,044,948 B2 | 5/2006 | Keppel | | 7,442,194 B2 | 10/2008 | Dumbauld et al. |
| 7,052,496 B2 | 5/2006 | Yamauchi | | 7,445,621 B2 | 11/2008 | Dumbauld et al. |
| D525,361 S | 7/2006 | Hushka | | 7,458,972 B2 | 12/2008 | Keppel |
| 7,070,597 B2 | 7/2006 | Truckai et al. | | 7,473,253 B2 | 1/2009 | Dycus et al. |
| 7,083,618 B2 | 8/2006 | Couture et al. | | 7,481,810 B2 | 1/2009 | Dumbauld et al. |
| 7,083,619 B2 | 8/2006 | Truckai et al. | | 7,491,201 B2 | 2/2009 | Shields et al. |
| 7,083,620 B2 | 8/2006 | Jahns et al. | | 7,491,202 B2 | 2/2009 | Odom et al. |
| 7,087,051 B2 | 8/2006 | Bourne et al. | | 7,668,597 B2 * | 2/2010 | Engmark et al. ............... 607/37 |
| 7,087,054 B2 | 8/2006 | Truckai et al. | | 2002/0013583 A1 | 1/2002 | Camran et al. |
| 7,090,673 B2 | 8/2006 | Dycus et al. | | 2002/0049442 A1 | 4/2002 | Roberts et al. |
| 7,090,689 B2 | 8/2006 | Nagase et al. | | 2002/0099372 A1 | 7/2002 | Schulze et al. |
| 7,101,371 B2 | 9/2006 | Dycus et al. | | 2002/0107517 A1 | 8/2002 | Witt et al. |
| 7,101,372 B2 | 9/2006 | Dycus et al. | | 2002/0111624 A1 | 8/2002 | Witt et al. |

| | | |
|---|---|---|
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0216733 A1* | 11/2003 | McClurken et al. ............ 606/51 |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0021026 A1* | 1/2005 | Baily ......................... 606/51 |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0141861 A1* | 6/2006 | Darley et al. ............... 439/587 |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0208289 A1* | 8/2008 | Darley et al. ................. 607/57 |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0082769 A1* | 3/2009 | Unger et al. ................. 606/52 |
| 2009/0088738 A1 | 4/2009 | Guerra et al. |
| 2009/0088739 A1 | 4/2009 | Hushka et al. |
| 2009/0088744 A1 | 4/2009 | Townsend |
| 2009/0088746 A1 | 4/2009 | Hushka et al. |
| 2009/0088747 A1 | 4/2009 | Hushka et al. |
| 2009/0088748 A1 | 4/2009 | Guerra et al. |

| | | | | | | |
|---|---|---|---|---|---|---|
| 2009/0088749 A1 | 4/2009 | Hushka et al. | | JP | 65-502328 | 3/1992 |
| 2009/0088750 A1 | 4/2009 | Hushka et al. | | JP | 5-5106 | 1/1993 |
| | | | | JP | 5-40112 | 2/1993 |
| FOREIGN PATENT DOCUMENTS | | | | JP | 06343644 A2 | 12/1994 |
| | | | | JP | 07265328 A2 | 10/1995 |
| DE | 2415263 | 10/1975 | | JP | 08056955 A2 | 3/1996 |
| DE | 2627679 | 1/1977 | | JP | 08252263 A2 | 10/1996 |
| DE | 3612646 | 4/1987 | | JP | 09010223 A2 | 1/1997 |
| DE | 8712328 | 3/1988 | | JP | 11244298 A2 | 9/1999 |
| DE | 4303882 | 8/1994 | | JP | 2000-342599 A2 | 12/2000 |
| DE | 19515914 | 7/1996 | | JP | 2000-350732 A2 | 12/2000 |
| DE | 29616210 | 1/1997 | | JP | 2001-008944 A2 | 1/2001 |
| DE | 19608716 | 4/1997 | | JP | 2001-029356 A2 | 2/2001 |
| DE | 19751106 | 5/1998 | | JP | 2001-128990 A2 | 5/2001 |
| DE | 19751108 | 5/1999 | | SU | 401367 | 11/1974 |
| DE | 19738457 | 1/2009 | | WO | WO 89/00757 | 1/1989 |
| EP | 0364216 | 4/1990 | | WO | WO 92/04873 | 4/1992 |
| EP | 0518230 | 12/1992 | | WO | WO 92/06642 | 4/1992 |
| EP | 0541930 | 5/1993 | | WO | WO 94/08524 | 4/1994 |
| EP | 0572131 | 12/1993 | | WO | WO 94/20025 | 9/1994 |
| EP | 0584787 | 3/1994 | | WO | WO 95/02369 | 1/1995 |
| EP | 0589453 | 3/1994 | | WO | WO 95/07662 | 3/1995 |
| EP | 0589555 | 3/1994 | | WO | WO 95/15124 | 6/1995 |
| EP | 0623316 | 11/1994 | | WO | WO 96/05776 | 2/1996 |
| EP | 0624348 | 11/1994 | | WO | WO 96/22056 | 7/1996 |
| EP | 0650701 | 5/1995 | | WO | WO 96/13218 | 9/1996 |
| EP | 0694290 | 3/1996 | | WO | WO 97/00646 | 1/1997 |
| EP | 0717966 | 6/1996 | | WO | WO 97/00647 | 1/1997 |
| EP | 0754437 | 3/1997 | | WO | WO 97/10764 | 3/1997 |
| EP | 0517243 | 9/1997 | | WO | WO 97/24073 | 7/1997 |
| EP | 0853922 | 7/1998 | | WO | WO 97/24993 | 7/1997 |
| EP | 0875209 | 11/1998 | | WO | WO 98/27880 | 7/1998 |
| EP | 0878169 | 11/1998 | | WO | WO 99/03407 | 1/1999 |
| EP | 0887046 | 1/1999 | | WO | WO 99/03408 | 1/1999 |
| EP | 0923907 | 6/1999 | | WO | WO 99/03409 | 1/1999 |
| EP | 0986990 | 3/2000 | | WO | WO 99/12488 | 3/1999 |
| EP | 1034747 | 9/2000 | | WO | WO 99/23933 | 5/1999 |
| EP | 1034748 | 9/2000 | | WO | WO 99/40857 | 8/1999 |
| EP | 1025807 | 10/2000 | | WO | WO 99/40861 | 8/1999 |
| EP | 1034746 | 10/2000 | | WO | WO 99/51158 | 10/1999 |
| EP | 1050278 | 11/2000 | | WO | WO 99/66850 | 12/1999 |
| EP | 1053719 | 11/2000 | | WO | WO 00/24330 | 5/2000 |
| EP | 1053720 | 11/2000 | | WO | WO 00/24331 | 5/2000 |
| EP | 1055399 | 11/2000 | | WO | WO 00/36986 | 6/2000 |
| EP | 1055400 | 11/2000 | | WO | WO 00/41638 | 7/2000 |
| EP | 1080694 | 3/2001 | | WO | WO 00/47124 | 8/2000 |
| EP | 1082944 | 3/2001 | | WO | WO 00/53112 | 9/2000 |
| EP | 1159926 | 12/2001 | | WO | WO 01/17448 | 3/2001 |
| EP | 1177771 | 2/2002 | | WO | WO 01/54604 | 8/2001 |
| EP | 1301135 | 4/2003 | | WO | WO 02/07627 | 1/2002 |
| EP | 1330991 | 7/2003 | | WO | WO 02/067798 | 9/2002 |
| EP | 1486177 | 6/2004 | | WO | WO 02/080783 | 10/2002 |
| EP | 1472984 | 11/2004 | | WO | WO 02/080784 | 10/2002 |
| EP | 0774232 | 1/2005 | | WO | WO 02/080785 | 10/2002 |
| EP | 1527747 | 5/2005 | | WO | WO 02/080786 | 10/2002 |
| EP | 1530952 | 5/2005 | | WO | WO 02/080793 | 10/2002 |
| EP | 1532932 | 5/2005 | | WO | WO 02/080794 | 10/2002 |
| EP | 1535581 | 6/2005 | | WO | WO 02/080795 | 10/2002 |
| EP | 1609430 | 12/2005 | | WO | WO 02/080796 | 10/2002 |
| EP | 1632192 | 3/2006 | | WO | WO 02/080797 | 10/2002 |
| EP | 1642543 | 4/2006 | | WO | WO 02/080798 | 10/2002 |
| EP | 1645238 | 4/2006 | | WO | WO 02/080799 | 10/2002 |
| EP | 1645240 | 4/2006 | | WO | WO 02/081170 | 10/2002 |
| EP | 1649821 | 4/2006 | | WO | WO 03/061500 | 7/2003 |
| EP | 1707143 | 10/2006 | | WO | WO 03/090630 | 11/2003 |
| EP | 1769765 | 4/2007 | | WO | WO 03/101311 | 12/2003 |
| EP | 1769766 | 4/2007 | | WO | WO 2004/032776 | 4/2004 |
| EP | 1929970 | 6/2008 | | WO | WO 2004/032777 | 4/2004 |
| EP | 1683496 | 12/2008 | | WO | WO 2004/052221 | 6/2004 |
| GB | 623316 | 5/1949 | | WO | WO 2004/073488 | 9/2004 |
| GB | 2214430 A | 6/1989 | | WO | WO 2004/073490 | 9/2004 |
| GB | 2213416 A | 8/1989 | | WO | WO 2004/073753 | 9/2004 |
| JP | 61-501068 | 9/1984 | | WO | WO 2004/082495 | 9/2004 |

| | | |
|---|---|---|
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.

Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended- EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.

* cited by examiner

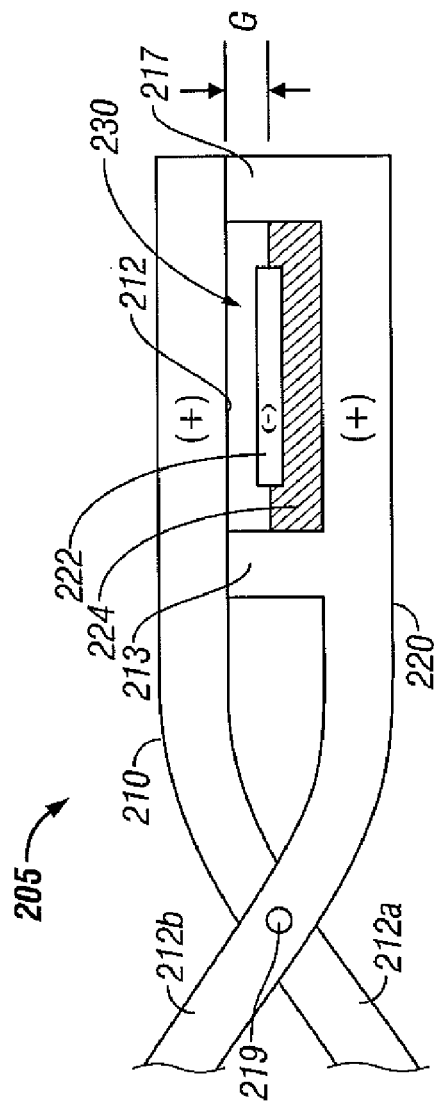
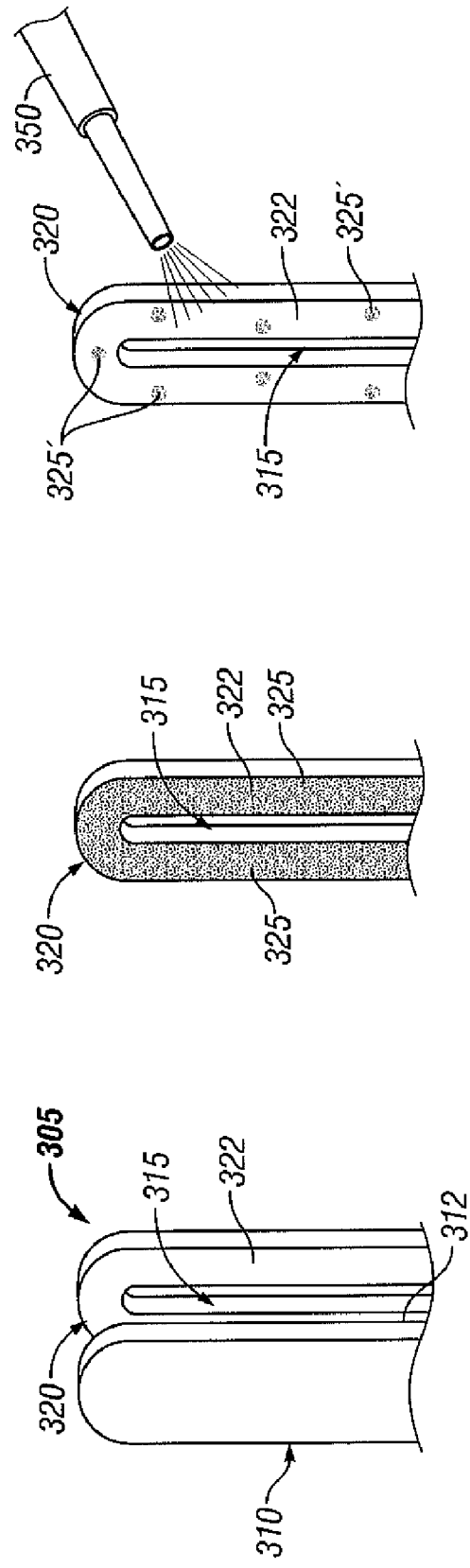
FIG. 2
FIG. 3A
FIG. 3B
FIG. 3C

METHOD OF MANUFACTURING END EFFECTOR ASSEMBLY FOR SEALING TISSUE

CROSS REFERENCE TO RELATED APPLICATION

This application claims the benefit of priority to U.S. Provisional Application Ser. No. 60/994,551 entitled "TISSUE SEALER AND END EFFECTOR ASSEMBLY AND METHOD OF MANUFACTURING SAME" filed Sep. 20, 2007 by Unger et al., the entire contents of which being incorporated by reference herein.

BACKGROUND

The present disclosure relates to an electrosurgical instrument and method for performing electrosurgical procedures. More particularly, the present disclosure relates to an open or endoscopic bipolar electrosurgical forceps and method of manufacturing an end effector assembly having stop members associated with one or both of a pair of opposing jaw members. The stop members are designed to control the gap distance between opposing jaw members and enhance the manipulation and gripping of tissue during the sealing process.

TECHNICAL FIELD

Forceps utilize mechanical action to constrict, grasp, dissect and/or clamp tissue. Electrosurgical forceps utilize both mechanical clamping action and electrical energy to effect hemostasis by heating the tissue and blood vessels. By controlling the intensity, frequency and duration of the electrosurgical energy applied through the jaw members to the tissue, the surgeon can coagulate, cauterize and/or seal tissue.

In order to effect a proper seal with larger vessels or thick tissue, two predominant mechanical parameters must be accurately controlled: the pressure applied to the tissue and the gap distance between the electrodes. As can be appreciated, both of these parameters are affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness, which is an indication of a good seal. It has been determined that fused tissue is optimum between about 0.001 inches to about 0.006 inches for small vessels and tissues and about 0.004 inches to about 0.010 inches for large, soft tissue structures. Below these ranges, the seal may shred or tear and above this range the tissue may not be properly or effectively sealed.

It is thought that the process of coagulating or cauterizing small vessels is fundamentally different than electrosurgical vessel or tissue sealing. "Vessel sealing" or "tissue sealing" is defined as the process of liquefying the collagen, elastin and ground substances in the tissue so that it reforms into a fused mass with significantly-reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them; however, larger vessels or tissue need to be "sealed" to assure permanent closure.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue which, if used for sealing purposes, would result in an ineffective or non-uniform seal. Other instruments generally rely on clamping pressure alone to procure proper sealing thickness and are often not designed to take into account gap tolerances and/or parallelism and flatness requirements, which are parameters that, if properly controlled, can assure a consistent and effective tissue seal.

Recently, instruments have been developed that utilize technology to form a vessel seal utilizing a unique combination of pressure, gap distance between opposing surfaces and electrical control to effectively seal tissue or vessels. Heretofore, a series of so-called stop members have been applied to the inner-facing, opposing tissue engaging surfaces to maintain a gap distance between opposing sealing surfaces of about 0.001 inches to about 0.010 inches. Typically, the stop members were sprayed atop the tissue engaging surfaces in various patterns by plasma deposition or other similar processes to assure proper parallelism when the jaw members were closed about tissue. In other instances, key-like gap plugs were employed to allow a user or manufacturer to selectively alter the size and shape of the stop members for a particular surgical purpose as described in U.S. Pat. No. 7,118,570. In yet other instances, a variable stop member is used that may be selectively adjusted to regulate the gap distance for particular tissue types and/or particular surgical purposes as described in U.S. patent application Ser. No. 10/846,262.

SUMMARY

The present disclosure relates to a bipolar forceps for sealing which includes at least one shaft having an end effector assembly disposed at a distal end thereof. The end effector assembly has a pair of first and second opposing jaw members which are movable relative to one another from a first position wherein the jaw members are disposed in spaced relation relative to one another to a second position wherein the jaw members cooperate to grasp tissue therebetween. The first jaw member includes proximal and distal ends which define a cavity along a length thereof which houses an insulative member therein. The insulative member has an electrically conductive sealing surface mounted thereto that is positioned to reside in substantial opposition with a second electrically conductive sealing surface disposed on the second jaw member. At least one of the proximal and distal ends extends a fixed distance toward the second jaw member such that the end and the second jaw member form a gap between electrically conductive surfaces when the jaw members are closed to grasp tissue.

In one embodiment, the gap between electrically conductive surfaces is in the range of about 0.001 inches to about 0.010 inches. In another embodiment, the first electrically conductive sealing plate is connected to a first electrical potential from an electrosurgical energy source and the second electrically conductive sealing plate and both the first and second jaw members are connected to a second electrical potential from the electrosurgical energy source.

The present disclosure also relates to a method for manufacturing an end effector assembly for sealing tissue and includes the steps of: providing a pair of first and second jaw members each including an inwardly facing electrically conductive sealing surface; and coating the inwardly facing electrically conductive sealing surface of at least one of the jaw members with an insulative material having a thickness within the range of about 0.001 inches to about 0.010 inches. The electrically conductive sealing surface may include a knife channel defined therealong.

The method also includes the steps of: allowing the insulative material to cure onto the inwardly facing electrically conductive sealing surface; and trimming the insulative material from the inwardly facing electrically conductive sealing surface to form a series of stop members arranged thereacross. The pair of first and second jaw members is then assembled about a pivot such that the two inwardly facing electrically conductive sealing surfaces are substantially opposed to each other in pivotal relation relative to one another. The step of trimming may involve laser etching and the coating step may involve plasma deposition and/or pad printing.

The present disclosure also relates to a method for manufacturing an end effector assembly for sealing tissue and includes the initial step of providing a pair of first and second jaw members each having an outer insulative housing and an electrically conductive tissue sealing surface. The jaw members are moveable relative to one another from a first position wherein the jaw members are disposed in spaced relation relative to one another to a second position wherein the jaw members cooperate to grasp tissue therebetween. The method also includes the steps of disposing a series of insulative stop members atop the insulative housing of one (or both) jaw member and forming a corresponding series of apertures within the electrically conductive sealing plate of the jaw member in vertical registry with the stop members.

The method further includes the steps of: aligning the electrically conductive sealing plate of the jaw member atop the insulative housing such that each of the series of stop members are received through a respective aperture within the electrically conductive sealing plate; and securing the electrically conductive sealing plate of the jaw member atop the insulative housing of the jaw member such that the stop members project from the electrically conductive sealing plate a distance of about 0.001 inches to about 0.010 inches. The pair of jaw members is then assembled about a pivot such that the respective electrically conductive sealing surfaces are substantially opposed to each other in pivotal relation relative to one another.

The present disclosure also relates to a method for manufacturing an end effector assembly for sealing tissue and includes the steps of: providing a pair of first and second jaw members each having an electrically conductive tissue sealing surface and being moveable relative to one another from a first position wherein the jaw members are disposed in spaced relation relative to one another to a second position wherein the jaw members cooperate to grasp tissue therebetween. At least one of the electrically conductive tissue sealing surfaces of one of the jaw members includes a series of cavities defined therein. The method also includes the steps of: providing a substantially liquefied insulative material from a source; and dispersing an amount (e.g., a dollop) of the insulative material into at least one of the cavities to form a stop member which projects a distance of about 0.001 inches to about 0.010 inches from the electrically conductive tissue sealing surface.

The method further includes the steps of: allowing the insulative material to cure atop the electrically conductive sealing surface; and assembling the pair of first and second jaw members about a pivot such that the electrically conductive surfaces are substantially opposed to each other in pivotal relation relative to one another. In one particular embodiment, the series of cavities are generally key-shaped.

The present disclosure also relates to a method for manufacturing an end effector assembly for sealing tissue and includes the steps of: providing first and second electrically conductive sealing plates; encasing at least one of the sealing plates in a insulative material; applying a load to the sealing plates; melting the insulative material via a solvent or heat source; allowing a gap to form within the range of about 0.001 inches to about 0.010 inches between the sealing plates; and removing the heat source to allow the insulative material to cure.

The present disclosure also relates to a method for manufacturing an end effector assembly for sealing tissue and includes the steps of: providing first and second electrically conductive sealing plates; encasing at least one of the electrically conductive sealing plates in a substantially moldable insulative material; applying a load to the electrically conductive sealing plates; allowing the insulative material to deform to create a gap between the sealing plates between about 0.001 inches to about 0.010 inches; and allowing the insulative material to cure. The moldable insulative material may include a material that changes in density and/or volume upon application of heat, chemicals, energy or combinations thereof.

BRIEF DESCRIPTION OF THE DRAWINGS

Various embodiments of the present disclosure are described herein with reference to the drawings wherein:

FIG. 2 is a schematic, side view of a bipolar forceps according to an embodiment of the present disclosure having a recessed electrically conductive sealing surface that provides the requisite gap distance between sealing surfaces;

FIGS. 3A-3D are enlarged, top views showing one envisioned method of forming stop members on electrically conductive surfaces of a jaw member according to the present disclosure;

DETAILED DESCRIPTION

Figure 1A:
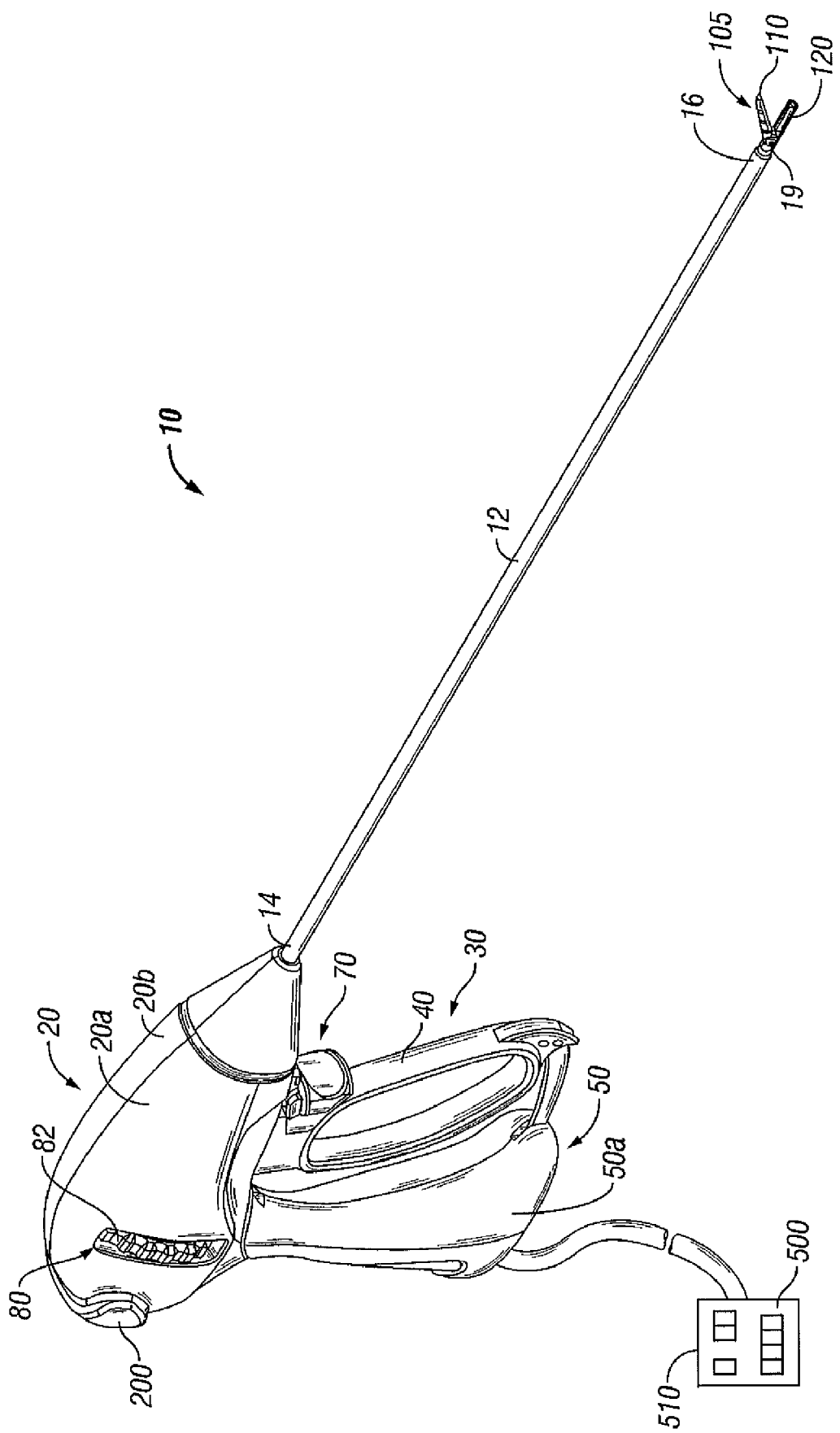
FIG. 1A is a right, perspective view of an endoscopic bipolar forceps according to the present disclosure having a housing, a shaft and a pair of jaw members affixed to a distal end thereof, the jaw members including an electrode assembly disposed therebetween.
Figure 1B:
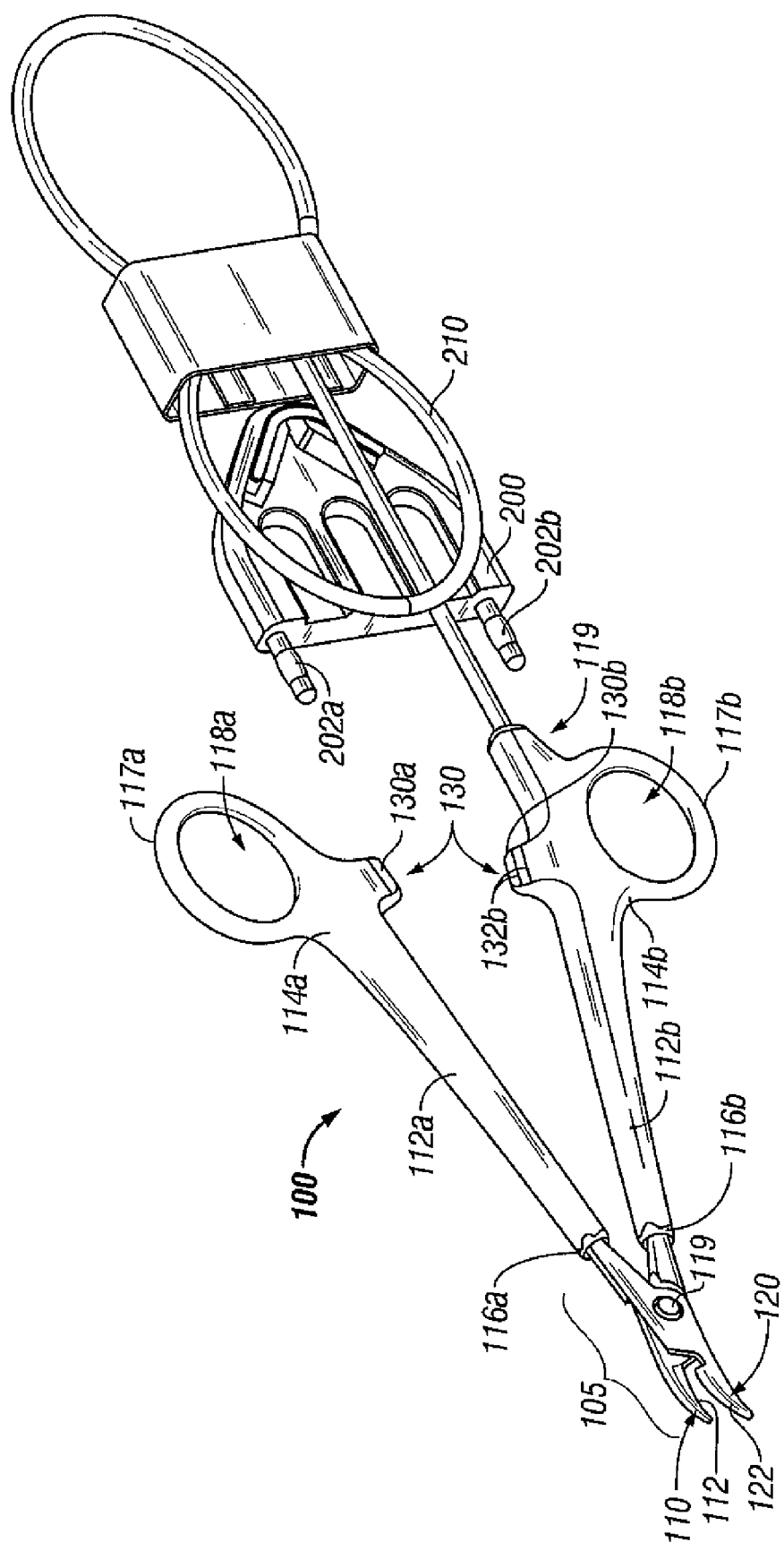
FIG. 1B is a left, perspective view of an open bipolar forceps according to the present disclosure showing a pair of first and second shafts each having a jaw member affixed to a distal end thereof with an electrode assembly disposed therebetween.
Figure 3D:
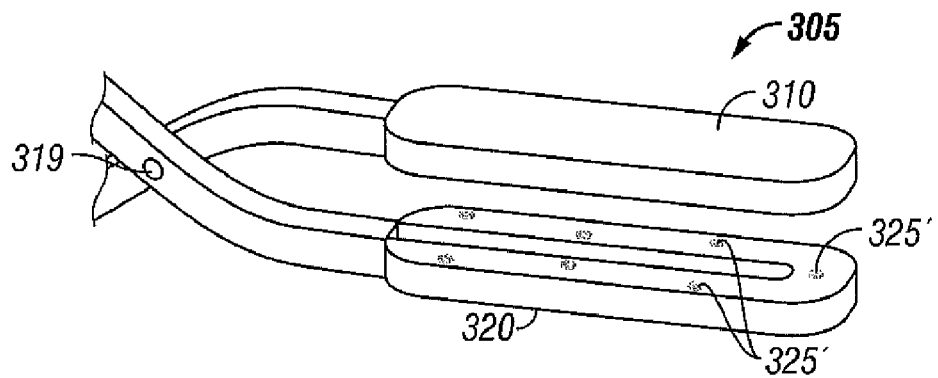

Referring now to FIGS. 1A and 1B, FIG. 1A depicts a bipolar forceps 10 for use in connection with endoscopic surgical procedures and FIG. 1B depicts an open forceps 100 contemplated for use in connection with traditional open surgical procedures. For the purposes herein, either an endoscopic instrument or an open instrument may be utilized with the end effector assembly described herein. Obviously, different electrical and mechanical connections and considerations apply to each particular type of instrument; however, the novel aspects with respect to the end effector assembly and its operating characteristics remain generally consistent with respect to both the open or endoscopic designs.

FIG. 1A shows a bipolar forceps 10 for use with various endoscopic surgical procedures and generally includes a housing 20, a handle assembly 30, a rotating assembly 80, a switch assembly 70 and an end effector assembly 105 having opposing jaw members 110 and 120 which mutually cooperate to grasp, seal and divide tubular vessels and vascular tissue. More particularly, forceps 10 includes a shaft 12 which has a distal end 16 dimensioned to mechanically engage the end effector assembly 105 and a proximal end 14 which mechanically engages the housing 20. The shaft 12 may include one or more known mechanically engaging components which are designed to securely receive and engage the end effector assembly 105 such that the jaw members 110 and 120 are pivotable relative to one another to engage and grasp tissue therebetween.

The proximal end 14 of shaft 12 mechanically engages the rotating assembly 80 (not shown) to facilitate rotation of the end effector assembly 105. In the drawings and in the descriptions which follow, the term "proximal", as is traditional, will refer to the end of the forceps 10 which is closer to the user, while the term "distal" will refer to the end which is further from the user. Details relating to the mechanically cooperating components of the shaft 12 and the rotating assembly 80 are described in commonly-owned U.S. patent application Ser. No. 10/460,926 entitled "VESSEL SEALER AND DIVIDER FOR USE WITH SMALL TROCARS AND CANNULAS".

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the end effector assembly 105 as explained in more detail below. Movable handle 40 and switch assembly 70 are preferably of unitary construction and are operatively connected to the housing 20 and the fixed handle 50 during the assembly process. Housing 20 is preferably constructed from two components halves 20a and 20b which are assembled about the proximal end of shaft 12 during assembly. Switch assembly is configured to selectively provide electrical energy to the end effector assembly 105.

As mentioned above, end effector assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 1B, an open forceps 100 includes a pair of elongated shaft portions 112a and 112b each having a proximal end 114a and 114b, respectively, and a distal end 116a and 116b, respectively. The forceps 100 includes jaw members 120 and 110 which attach to distal ends 116a and 116b of shafts 112a and 112b, respectively. The jaw members 110 and 120 are connected about pivot pin 119 which allows the jaw members 110 and 120 to pivot relative to one another from the first to second positions for treating tissue. The end effector assembly 105 is connected to opposing jaw members 110 and 120 and may include electrical connections through or around the pivot pin 119. Examples of various electrical connections to the jaw members are shown in commonly-owned U.S. patent application Ser. Nos. 10/474,170, 10/116, 824, 10/284,562 and 10/369,894, and U.S. Pat. Nos. 7,101, 372, 7,083,618 and 7,101,371.

Each shaft 112a and 112b includes a handle 117a and 117b disposed at the proximal end 114a and 114b thereof which each define a finger hole 118a and 118b, respectively, therethrough for receiving a finger of the user. As can be appreciated, finger holes 118a and 118b facilitate movement of the shafts 112a and 112b relative to one another which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 is preferably included for selectively locking the jaw members 110 and 120 relative to one another at various positions during pivoting.

More particularly, the ratchet 130 includes a first mechanical interface 130a associated with shaft 112a and a second mating mechanical interface associated with shaft 112b. Each position associated with the cooperating ratchet interfaces 130a and 130b holds a specific, i.e., constant, strain energy in the shaft members 112a and 112b which, in turn, transmits a specific closing force to the jaw members 110 and 120. It is envisioned that the ratchet 130 may include graduations or other visual markings which enable the user to easily and quickly ascertain and control the amount of closure force desired between the jaw members 110 and 120.

As best seen in FIG. 1B, forceps 100 also includes an electrical interface or plug 200 which connects the forceps 100 to a source of electrosurgical energy, e.g., an electrosurgical generator (not shown). Plug 200 includes at least two prong members 202a and 202b which are dimensioned to mechanically and electrically connect the forceps 100 to the electrosurgical generator 500 (See FIG. 1A). An electrical cable 210 extends from the plug 200 and securely connects the cable 210 to the forceps 100. Cable 210 is internally divided within the shaft 112b to transmit electrosurgical energy through various electrical feed paths to the end effector assembly 105.

One of the shafts, e.g., 112b, includes a proximal shaft connector/flange 119 which is designed to connect the forceps 100 to the electrosurgical energy source 500. More particularly, flange 119 mechanically secures electrosurgical cable 210 to the forceps 100 such that the user may selectively apply electrosurgical energy as needed.

The jaw members 110 and 120 of both the endoscopic version of FIG. 1A and the open version of FIG. 1B are generally symmetrical and include similar component features which cooperate to permit facile rotation about pivot 19, 119 to effect the grasping and sealing of tissue. Each jaw member 110 and 120 includes an electrically conductive tissue contacting surface 112 and 122, respectively, which cooperate to engage tissue during sealing and cutting.

The various electrical connections of the end effector assembly 105 are preferably configured to provide electrical continuity to the electrically conductive tissue contacting surfaces 112 and 122 through the end effector assembly 105. For example, a series of cable leads may be configured to carry different electrical potentials to the conductive surfaces 112 and 122. Commonly owned U.S. patent application Ser. Nos. 10/474,170, 10/116,824 and 10/284,562 all disclose various types of electrical connections which may be made to the conductive surfaces 112 and 122 through one or both of the shaft 112a and 112b. In addition, and with respect to the types of electrical connections that may be made to the jaw members 110 and 120 for endoscopic purposes, commonly-owned U.S. patent application Ser. No. 10/369,894 and U.S. Pat. Nos. 7,101,372, 7,083,618 and 7,101,371 all disclose other types of electrical connections.

FIG. 2 shows one embodiment of an end effector assembly 205 for use with a bipolar forceps 10, 100 for sealing tissue that includes shafts 212a and 212b rotatable about a common pivot 219. The end effector assembly 205 has a pair of first and second opposing jaw members 210 and 220 that are selectively movable relative to one another from a first position wherein the jaw members 210, 220 are disposed in spaced relation relative to one another to a second position wherein the jaw members 210, 220 cooperate to grasp tissue therebetween. The first jaw member 220 includes a cavity or recess 230 defined therein that extends along a length thereof. The cavity 230 is dimensioned to house an insulative member 224 between respective proximal and distal ends 213 and 217. The insulative member 224 has an electrically conductive sealing surface 222 mounted thereto that is positioned to reside in substantial vertical opposition with a second electrically conductive sealing surface 212 disposed on the second jaw member 210.

Ends 213 and 217 of jaw member 220 extend a fixed distance toward the second jaw member 210 such that the ends 213 and 217 and the second jaw member 210 form a gap "G" between electrically conductive surfaces 212 and 222 when the jaw members 210 and 220 are closed to grasp tissue. As mentioned above, two mechanical factors play an important role in determining the resulting thickness of the sealed tissue and effectiveness of a tissue seal, e.g., the pressure applied between opposing jaw members 210 and 220 and the gap distance "G" between the opposing tissue contacting surfaces 212 and 222 during the sealing process. With particular respect to vessels and small tissue bundles, a gap distance "G" during sealing within the range of about 0.001 inches to about 0.010 inches is particularly suitable for effectively sealing tissue. Other gap ranges may be preferable with other tissue types such as bowel or large vascular structures. A working pressure within the range of about 3 kg/cm$^2$ to about 16 kg/cm$^2$ between sealing surfaces 212 and 222 has been shown to be effective for sealing various tissue types.

Electrically conductive sealing surface 222 is coupled to a first electrical potential from an electrosurgical energy source, e.g., generator 500 (see FIG. 1A), and sealing plate 212 and jaw members 220 are coupled a second electrical potential from the electrosurgical energy source. In use, tissue is initially grasped between jaw members 210 and 220 and positioned within cavity 230. The shaft members 212a and 212b are pivoted to close the jaw members 210 and 220 about the tissue under a pressure within the above working range. As mentioned above, ends 213 and 217 are dimensioned to maintain a gap distance "G" between the sealing surfaces 212 and 222 such that upon activation, electrosurgical energy travels between the different electrical potentials to form an effective tissue seal between sealing surfaces 212 and 222. Jaw member 220 may be configured such that only one end, e.g., proximal end 213, is dimensioned to maintain the requisite gap distance between sealing surfaces 212 and 222.

FIGS. 3A-3D show one method for manufacturing an end effector assembly 305 for sealing tissue according to the present disclosure and includes the initial step of providing a pair of jaw members 310 and 320 each including an inwardly facing electrically conductive sealing surface 312 and 322. The method also includes the steps of: coating the inwardly facing electrically conductive sealing surface 322 of at least one of the jaw members, e.g., jaw member 320, with an insulative material or substrate 325 having a thickness within the range of about 0.001 inches to about 0.010 inches; and allowing the insulative material to cure onto the inwardly facing electrically conductive sealing surface 322. Once cured, the method includes the step of trimming the insulative material 325 from the inwardly facing electrically conductive sealing surface 322 to form a series of stop members 325' arranged thereacross. A laser 350 (or other suitable etching or removal tool) may be utilized to etch or form the stop members 325'. The pair of first and second jaw members 310 and 320 are then assembled about a pivot 319 such that the two inwardly facing electrically conductive sealing surfaces 312 and 322 are substantially opposed to each other in pivotal relation relative to one another.

In one embodiment, the step of trimming may involve laser etching and the coating step may involve plasma deposition and/or pad printing. One or both of the electrically conductive sealing surfaces 312 and 322 may include a knife channel defined therealong for reciprocating a knife (not shown) therein for cutting tissue.

Figure 4A:
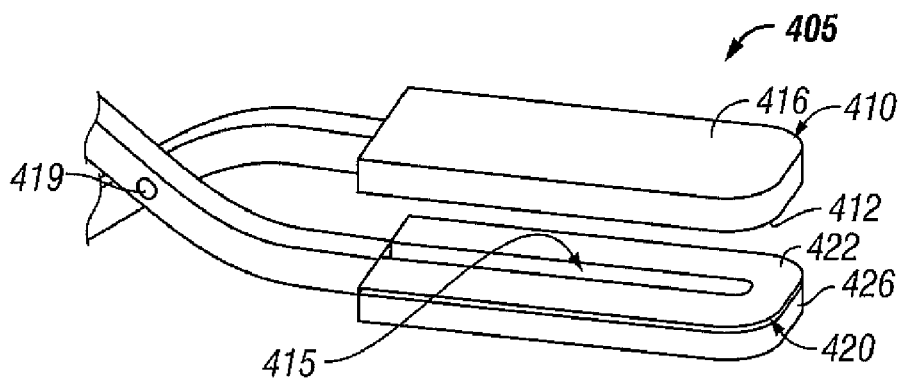
FIGS. 4A-4C are enlarged, perspective views showing another envisioned method of forming stop members on electrically conductive surfaces of a jaw member according to the present disclosure.
Figure 4B:
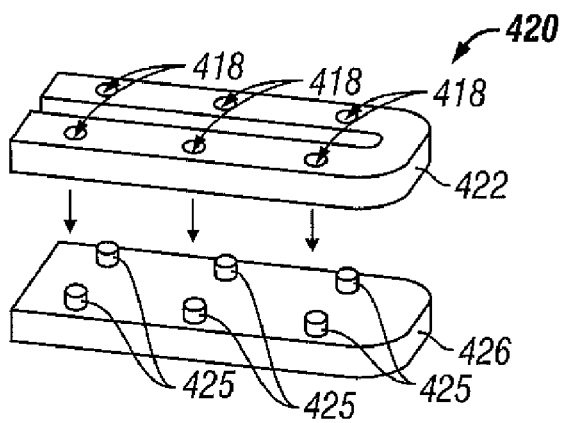
Figure 4C:
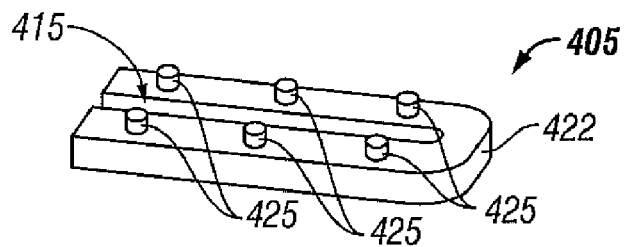

FIGS. 4A-4C show yet another method for manufacturing an end effector assembly 405 for sealing tissue according to the present disclosure and includes the initial step of providing a pair of first and second jaw members 410 and 420 each having an outer insulative housing 416 and 426 and an electrically conductive tissue sealing plate 412 and 422, respectively. The jaw members 410 and 420 are moveable relative to one another about a pivot 419 from a first position wherein the jaw members 410 and 420 are disposed in spaced relation relative to one another to a second position wherein the jaw members 410 and 420 cooperate to grasp tissue therebetween. The method also includes the steps of disposing a series of insulative stop members 425 atop an insulative substrate of at least one of the jaw members, e.g., jaw member 420, and forming a corresponding series of apertures 418 within the electrically conductive sealing plate 422 of the jaw member 420 in vertical registry with the stop members 425.

The method further includes the steps of: aligning the electrically conductive sealing plate 422 of the jaw member 420 atop the insulative substrate 426 such that each of the series of stop members 425 is received through a respective aperture 418 within the electrically conductive sealing plate 422; and securing the electrically conductive sealing plate 422 atop the insulative substrate 426 such that the stop members 425 project from the electrically conductive sealing plate 422 a distance within the range of about 0.001 inches to about 0.010 inches. The pair of jaw members 410 and 420 is then assembled about pivot 419 such that the respective electrically conductive surfaces 412 and 422 are substantially opposed to each other in pivotal relation relative to one another.

Figure 5A:
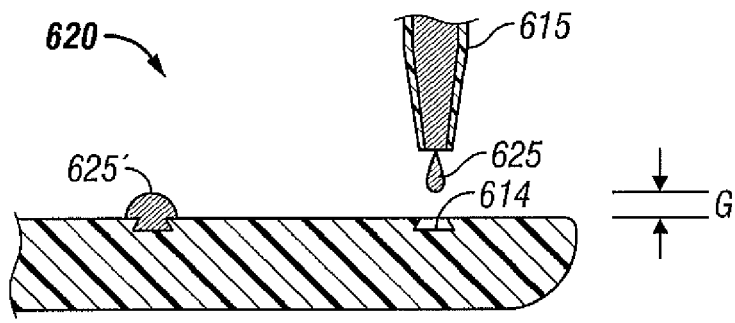
FIGS. 5A-5B is an enlarged, side view showing yet another envisioned method of forming stop members on electrically conductive surfaces of a jaw member according to the present disclosure.
Figure 5B:
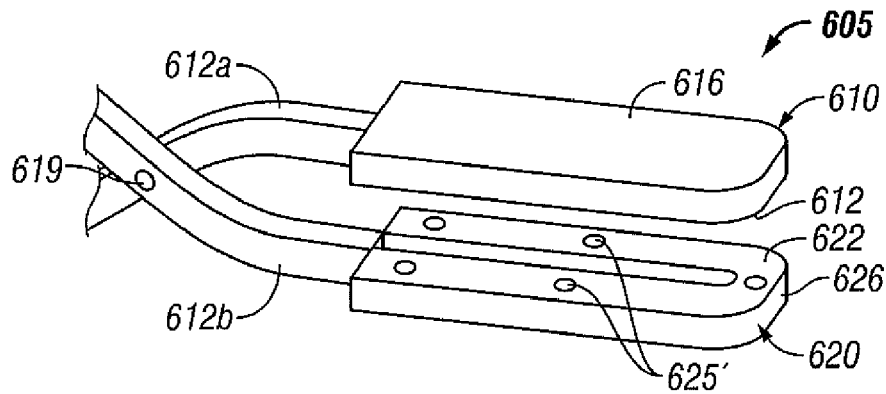

FIGS. 5A and 5B show yet another method for manufacturing an end effector assembly 605 for sealing tissue according to the present disclosure and includes the initial step of providing a pair of first and second jaw members 610 and 620 each having an electrically conductive tissue sealing surface 612 and 622, respectively. The jaw members 610 and 620 are moveable relative to one another from a first position wherein the jaw members 610 and 620 are disposed in spaced relation relative to one another to a second position wherein the jaw members 610 and 620 cooperate to grasp tissue therebetween. At least one of the electrically conductive tissue sealing surfaces, e.g., surface 622, includes a series of cavities 614 defined therein. The method also includes the steps of: providing a substantially liquefied insulative material 625 from a source of liquefied insulative material 615; and dispersing an amount (e.g., a dollop) of the insulative material 625 into at least one of the cavities 614 of to form a stop member 625' that projects a distance of about 0.001 inches to about 0.010 inches from the electrically conductive tissue sealing surface 622.

The method further includes the steps of: allowing the stop member 625' to cure atop the electrically conductive sealing surface 622 and assembling the pair of first and second jaw members about a pivot 619 such that the electrically conductive surfaces 612 and 622 are substantially opposed to each other in pivotal relation relative to one another. In one particular embodiment, the series of cavities 614 are generally key-shaped. Other suitable geometric shapes are also envisioned that will provide secure engagement of the stop member 625' atop the sealing surface 622 once cured, e.g., polygonal, t-shaped, I-beam, etc.

Figure 6:
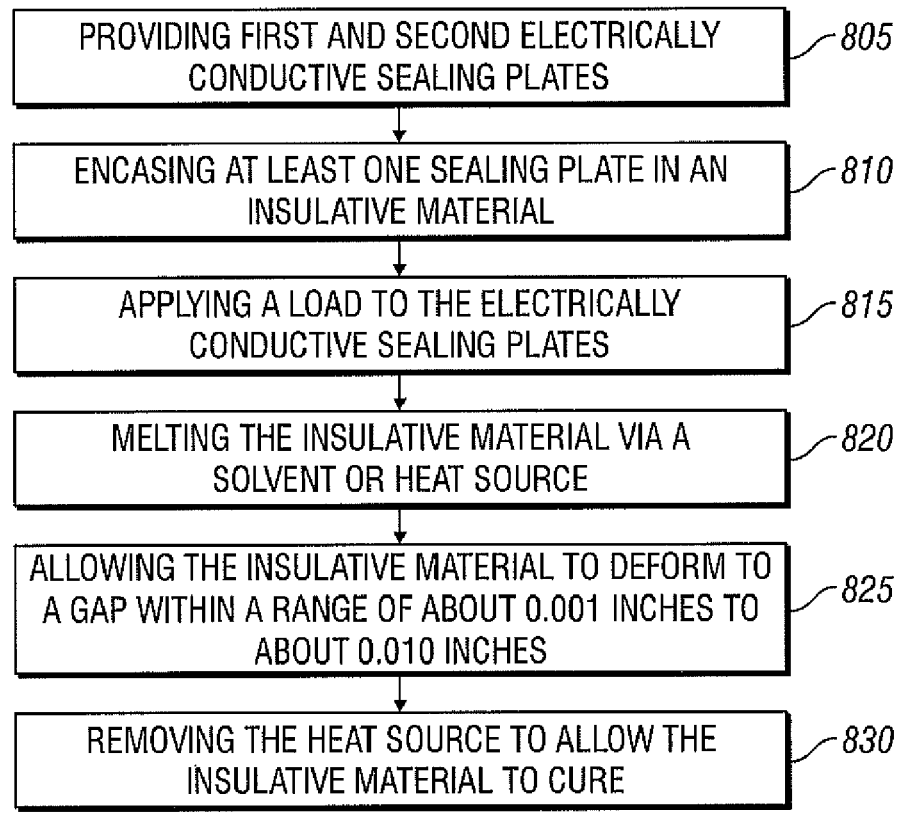
FIG. 6 is a flow diagram illustrating another method of manufacturing an end effector assembly according to the present disclosure.

FIG. 6 illustrates another method for manufacturing an end effector assembly for sealing tissue (not shown) and includes the initial step 805 of providing first and second electrically conductive sealing plates. Step 810 includes encasing at least one sealing plate in an insulative material. Step 815 includes applying a load to the electrically conductive sealing plates and step 820 includes melting the insulative material via a solvent or heat source. Step 825 includes allowing the insulative material to deform to a gap within a range of about 0.001 inches to about 0.010 inches between sealing plates. Step 830 includes removing the heat source to allow the insulative material to cure. One or both jaw members may be manufactured in this fashion and then assembled to create an end effector assembly for use with sealing tissue.

Another method according to the present disclosure relates to a method for manufacturing an end effector assembly for sealing tissue and includes the steps of: providing first and second electrically conductive sealing plates; encasing at least one of the electrically conductive sealing plates in a substantially moldable insulative material; applying a load to the electrically conductive sealing plates; allowing the insulative material to deform to create a gap between the sealing plates between about 0.001 inches to about 0.010 inches; and allowing the insulative material to cure. The moldable insulative material may include a material that changes in density and/or volume upon application of heat, chemicals, energy or combinations thereof.

From the foregoing and with reference to the various figure drawings, those skilled in the art will appreciate that certain modifications can also be made to the present disclosure without departing from the scope of the same. For example, forceps 10, 100 or any of the aforedescribed end effector assemblies 105, 305, 405, 505 or 605 may be designed such that the assembly is fully or partially disposable depending upon a particular purpose or to achieve a particular result. More particularly, end effector assembly 105 may be selectively and releasably engageable with the distal end 16 of the shaft 12 and/or the proximal end 14 of the shaft 12 may be selectively and releasably engageable with the housing 20 and handle assembly 30. In either of these two instances, the forceps 10 would be considered "partially disposable" or "reposable", i.e., a new or different end effector assembly 105 (or end effector assembly 105 and shaft 12) selectively replaces the old end effector assembly 105 as needed.

An insulator (not shown) may also be included to limit and/or reduce many of the known undesirable effects related to tissue sealing, e.g., flashover, thermal spread and stray current dissipation. At least one of the electrically conductive surfaces, e.g., 322, of one of the jaw members, e.g., 320, includes a longitudinally-oriented channel 315 defined therein (See FIG. 3A) that extends from the proximal end of the electrically conductive sealing surface 322 to the distal end. The channel 315 facilitates longitudinal reciprocation of a knife (not shown) along a preferred cutting plane to effectively and accurately separate the tissue along a formed tissue seal.

By controlling the intensity, frequency and duration of the electrosurgical energy applied to the tissue, the user can selectively seal tissue. The generator 500 may include a controller 510 (See FIG. 1A) that operatively couples to one or more sensors (not shown) that determine or measure tissue thickness, tissue moisture, tissue type, tissue impedance, etc. and automatically signal the controller 510 to adjust the electrosurgical energy prior to or during the sealing process to optimize the tissue seal.

The stop member(s) may be dimensioned in any suitable geometric configuration and may be disposed on or adjacent to one or both of the electrically conductive tissue sealing surfaces or operatively associated with one or both jaw members.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for manufacturing an end effector assembly for sealing tissue, comprising the steps of:
    providing first and second electrically conductive sealing plates;
    encasing at least one of the electrically conductive sealing plates in a substantially moldable insulative material;
    applying a load to the electrically conductive sealing plates;
    allowing the insulative material to deform to create a gap between the sealing plates between about 0.001 inches to about 0.010 inches; and
    allowing the insulative material to cure.

2. A method for manufacturing an end effector assembly for sealing tissue according to claim 1 wherein the moldable insulative material includes a material that changes in at least one of density and volume upon application of at least one of heat, chemicals, energy or combinations thereof.

3. A method for manufacturing an end effector assembly for sealing tissue, comprising the steps of:
    providing first and second electrically conductive sealing plates;
    encasing at least one of the electrically conductive sealing plates in a insulative material;
    applying a load to the electrically conductive sealing plates;
    heating the insulative material via a heat source;
    allowing the insulative material to deform to create a gap between the sealing plates between about 0.001 inches to about 0.010 inches; and
    allowing the insulative material to cure.

4. A method for manufacturing an end effector assembly for sealing tissue according to claim 3 wherein the heat source is a solvent.

* * * * *